(12) United States Patent
Nielsen

(10) Patent No.: US 9,199,057 B2
(45) Date of Patent: Dec. 1, 2015

(54) URINARY CATHETER ASSEMBLY

(75) Inventor: Henrik Lindenskov Nielsen, Smørum (DK)

(73) Assignee: Coloplast A/S, Humlebaek (DK)

( * ) Notice: Subject to any disclaimer, the term of this patent is extended or adjusted under 35 U.S.C. 154(b) by 192 days.

(21) Appl. No.: 13/992,762

(22) PCT Filed: Dec. 13, 2011

(86) PCT No.: PCT/DK2011/050478
§ 371 (c)(1),
(2), (4) Date: Jun. 10, 2013

(87) PCT Pub. No.: WO2012/079581
PCT Pub. Date: Jun. 21, 2012

(65) Prior Publication Data
US 2013/0261607 A1      Oct. 3, 2013

(30) Foreign Application Priority Data

Dec. 15, 2010 (DK) ................................ 2010 70549

(51) Int. Cl.
*A61M 25/00* (2006.01)
*A61M 25/01* (2006.01)
*A61M 25/08* (2006.01)
*A61B 19/02* (2006.01)
*A61B 17/08* (2006.01)

(52) U.S. Cl.
CPC .............. *A61M 25/00* (2013.01); *A61B 19/026* (2013.01); *A61M 25/002* (2013.01); *A61M 25/01* (2013.01); *A61M 25/0111* (2013.01); *A61M 25/0113* (2013.01); *A61B 2017/088* (2013.01); *A61M 25/0017* (2013.01)

(58) Field of Classification Search
CPC .............. A61M 25/002; A61M 25/00; A61M 25/0111; A61M 25/01; A61M 25/0113; A61M 25/0017; A61M 1/0078; A61B 19/026; A61B 2017/088; A61F 2/962; A61F 2/966
See application file for complete search history.

(56) References Cited

U.S. PATENT DOCUMENTS

| 3,537,451 | A | | 11/1970 | Beck et al. | |
|---|---|---|---|---|---|
| 3,648,704 | A | * | 3/1972 | Jackson | 604/172 |
| 4,563,171 | A | * | 1/1986 | Bodicky | 604/540 |
| 5,041,085 | A | * | 8/1991 | Osborne et al. | 604/541 |
| 5,356,390 | A | * | 10/1994 | Erskine | 604/165.02 |
| 5,507,728 | A | * | 4/1996 | Erskine | 604/165.02 |
| 2008/0097362 | A1 | * | 4/2008 | Mosler et al. | 604/349 |
| 2008/0208209 | A1 | * | 8/2008 | Fischer et al. | 606/108 |
| 2009/0043287 | A1 | * | 2/2009 | Mosler et al. | 604/544 |
| 2010/0211050 | A1 | * | 8/2010 | Luther | 604/544 |
| 2012/0221092 | A1 | * | 8/2012 | Jaffe et al. | 623/1.11 |
| 2012/0271281 | A1 | * | 10/2012 | Schertiger | 604/544 |

FOREIGN PATENT DOCUMENTS

| AU | 2008201719 | 5/2008 |
|---|---|---|
| GB | 322426 | 12/1929 |
| WO | 2005092419 | 10/2005 |

* cited by examiner

*Primary Examiner* — Adam Marcetich
(74) *Attorney, Agent, or Firm* — Coloplast Corp., Coloplast A/S; Nick Baumann

(57) ABSTRACT

A catheter assembly comprising a urinary catheter and a package with flexible walls is provided. Coupling means in form of a first coupling member on the catheter and a second coupling member on the package is further provided. The coupling means are in form of a protrusion or depression on the second coupling member and a matching depression or protrusion on the first coupling member. The user may move the catheter in and out of the package without touching the catheter itself, thus eliminating or minimizing the risk of contamination of the catheter.

6 Claims, 2 Drawing Sheets

URINARY CATHETER ASSEMBLY

The invention relates to a urinary catheter assembly which comprises a urinary catheter and a package. The urinary catheter has a first coupling member adapted for cooperation with a second coupling member at the package. Thereby, the catheter may be exited from the package by the coupling members.

BACKGROUND

Urinary catheter assemblies are generally known for providing a user with an easy to use assembly that allows the user to empty his/her urinary bladder in an easy and convenient way.

One of the most common drawbacks that affect a user of urinary catheters is an increased tendency of contracting a urinary tract infection as a side effect of inserting a foreign object into the urethra. One of the most critical issues which may concern the user when inserting a urinary catheter into the urethra is the need to maintain the insertable part of the catheter assembly as sterile as possible, in order to minimize the risk of contracting urinary tract infections. One of the methods used to reduce this risk has been to develop catheter assemblies, which ensures that the user can remove a catheter from its package and insert the catheter without having to touch the insertable part of the catheter assembly with the fingers of the hand prior or during the insertion of the catheter.

DESCRIPTION OF RELATED ART

Document WO 98/11932 discloses one way of allowing non-contaminated insertion of a catheter by providing a catheter package made of two layers of film which are welded along its periphery providing a peelable joint, allowing the two layers to be peeled off from each other for exposing the catheter from the package and the package may be used as an applicator to be gripped by the user. This way of enabling a non-contaminated insertion may be difficult for users that have reduced dexterity in their hands or fingers, as the separation of the layers may require fine movements.

Document WO 05/092419 discloses a catheter and a tubular package where the catheter may be extended out of the package without touching the insertable part of the catheter. The distal end of the catheter is provided with a metal and the outside of the package is provided with a magnet, where the movement of the magnet is transferred to the distal end of the catheter, allowing the catheter to be extended out of the package. Such a package may be seen as not being environmentally friendly for a single use catheter assembly as the catheter package contains metals in the form of a magnet and the magnetic part of the catheter.

SUMMARY OF THE INVENTION

The invention relates to a catheter assembly comprising a urinary catheter and a package with flexible walls. The catheter assembly is provided with coupling means in form of a first coupling member on the catheter and a second coupling member on the package. The coupling means are in form of a protrusion or depression on the second coupling member and a matching depression or protrusion on the first coupling member. The user may move the catheter in and out of the package without touching the catheter itself, thus eliminating or minimising the risk of contamination of the catheter. Furthermore, the catheter assembly may be seen as environmentally friendly.

DETAILED DESCRIPTION OF THE INVENTION

In a first aspect, the invention relates to a urinary catheter assembly comprising
  a urinary catheter having a proximal end for insertion into the urethra and a distal end comprising a first coupling member
  a catheter package comprising a tubular member having walls of a flexible material, and having a proximal end and a distal end defining a longitudinal axis of the catheter package where the flexible tubular member comprises a cavity for accommodation of the urinary catheter along the longitudinal axis of the catheter package and the catheter package and where the proximal end of the catheter package is arranged to allow for the exposure of the proximal end of the urinary catheter, and
  a second coupling member that is arranged on an outer surface of the catheter package wall
wherein the second coupling member is provided with coupling means for engaging the first coupling member through the flexible wall of the catheter package, so that the catheter may be manoeuvred along the longitudinal axis of the catheter package, where the coupling means are in form of a protrusion or a depression on the inner surface area which communicates with a matching depression or protrusion on the first coupling member.

The user may grab the tubular package with one hand and the second coupling member with the other hand and move the second coupling member relative to the catheter package along the longitudinal axis of the catheter package. This means that the catheter can be manoeuvred out of the end of the package during and/or prior to the insertion of the catheter into the urethra without having to come into direct contact with the insertable part of the catheter. When the insertable part of the catheter extends out of the package the user can hold on to the catheter package and use the catheter package to manoeuvre the insertable part of the catheter into the urethra.

Another advantage of the present invention is that the user may position the catheter assembly so that the insertion of the insertable part of the catheter may be performed while extending the catheter out of the package by positioning the proximal end of the tubular member close to the urethra and inserting the catheter by extending the catheter out of its package.

By allowing the catheter to be extended out of the package without having to touch the insertable part of the catheter, the insertion of the catheter may be performed in nearly any environment without the user having to prepare beforehand, for example by having to wash his/her hands or put on clean gloves, and still performing a catheter insertion under sterile conditions, or at least close to sterile conditions.

Furthermore, a catheter assembly according to the present invention allows the catheter to be retracted into the tubular member after insertion without having to touch the inserted or used part of the catheter, so as to keep the user's hands free from contamination of urine.

Yet further, by arranging the catheter assembly according to the present invention, the tubular member may be used as an extension to the insertable catheter allowing the user to divert the flow of urine from the distal end of the catheter to the distal end of the tubular member. This allows the user to position him- or herself at a distance from a toilet or a drainage facility, which will assist users that may have reduced dexterity such as para- or tetraplegics.

The coupling means between the first and second coupling members may be seen providing a mechanically match between the first and the second coupling member, so that any longitudinal movement of one coupling member is transferred to the other coupling member. This means that an external surface of the first coupling member which is in indirect contact with an internal surface of the second coupling member may be constructed in such a way that the first and the second coupling members may not separate along the longitudinal axis of the catheter package. Such a construction might be seen as a plug and socket configuration, where the first coupling member is enclosed by the second coupling member so that when the second coupling member is moved the mechanical matching of the coupling members causes the first coupling member to move along with the second coupling member, relative to the tubular member of the catheter package.

In one embodiment of the present invention, the second coupling member may be arranged to surround the tubular member in a direction that is perpendicular to the longitudinal axis of the catheter package. The indirect coupling between the first coupling member and the second coupling member, which occurs through the tubular member, may in some instances be dependent on the stiffness or integrity of the first and/or the second coupling member. Thus, by providing a second coupling member that surrounds the tubular member, it may be possible to construct a second coupling member that is rigid enough to provide a continuous and uninterrupted pressure to the first coupling member, during the movement of the two coupling members. Furthermore, a second coupling member that surrounds the tubular member may be easier to access by the user, in order to provide movement in the longitudinal direction of the catheter package.

In one embodiment, the first coupling means may be at least one inwardly radially extending protrusion extending from an inner surface of the second coupling member. Such a protrusion may be constructed to engage a portion of the first coupling member, where the protrusion may decrease the maximum diameter of the second coupling member and where the first coupling member has an outer area having a diameter that is larger than the maximum diameter of the second coupling means. Thus, the protrusion may engage a depression in the first coupling member, or the protrusion may engage an end part of the first coupling member or similar. This construction allows the second coupling member to transfer pressure to the first coupling member through the tubular member where the direction of the force may be in the longitudinal direction of the catheter package, and this transfer of pressure allows the first coupling member to move inside the tubular member or the catheter package as directed by the second coupling member.

In one embodiment, the first coupling means may be at least two inwardly radially extending protrusions extending substantially diametrically opposite each other from an inner surface of the second coupling member. By arranging the protrusions in said manner, the protrusions engage the first coupling member from opposite sides and may thereby reduce the risk that the first coupling member and the second coupling member may be disconnected from each other during the movement of the second coupling member. Furthermore, this allows the inner diameter of the second coupling member to be reduced in the direction where the protrusions are opposite each other, while maintaining a larger diameter in the direction which is substantially perpendicular in the radial direction to that of the protrusions. Such an arrangement allows the second coupling member to transfer pressure to certain areas of the first coupling member and not to be in communication with the first coupling member in any other areas. Thus, the amount of surface area of the second coupling member that communicates with the first coupling member through the tubular member is small and this arrangement may reduce the friction between the external surface of the tubular member and the inner surface of the second coupling member, which in turn reduces the forces needed to manoeuvre the second coupling member along the longitudinal axis of the catheter package.

In one embodiment of the present invention, a surface area of the second coupling member that is adjacent to the tubular member may be provided with a low friction surface. One of the issues which affects the ease of use of the catheter assembly according to the present invention is the frictional forces that occur between the inner surface of the second coupling member and the outer surface of the tubular member. High frictional forces or frictional coefficients between the two surface areas may result in the user having to apply a considerable amount of force to move the second coupling member along the longitudinal axis of the catheter package or the tubular member. This frictional force/coefficient may be reduced by having a smaller surface area, where the two surfaces are in contact with each other, while another method of solving this is by providing the inner surface of the second coupling member with a low frictional surface. Such a low frictional surface may be provided in the form of a hydrophilic coating, a Teflon™ coating, a wax coating or any kind of suitable surface treatment that reduces the frictional forces. Another way of reducing the friction may be to provide the second coupling member and/or the tubular member in materials that when in direct contact have a low frictional coefficient.

Another way of reducing the friction is to provide the tubular member with a similar surface area that has a reduced frictional coefficient, while maintaining at least a part of the surface area of the tubular member with a high frictional area where the user may grip the tubular member or the catheter package.

In one embodiment of the present invention, the friction between the tubular member and the second coupling member may be provided by applying a layer of friction reducing lubricant, e.g. silicone oil, on the outer surface of the tubular member, or a similar friction reducing lubricant. Alternatively, the friction reducing lubricant may be applied to the inner surface of the second coupling member so that the amount of lubricant may be reduced and the risk of the lubricant contaminating the fingers, hands, clothing, etc. is reduced, as the tubular member is not covered in a lubricious material. Yet further, both the tubular member and the inner surface of the second coupling member may be provided with a friction reducing lubricant.

The tubular member of the present invention may be provided in a material as disclosed in Danish patent applications PA 2010 70351 and PA 2010 70350, which are hereby incorporated by reference.

In one embodiment of the present invention, the first coupling member may be provided with a second coupling means that engage the first coupling means of the second coupling member. The second coupling means may be arranged to conform with the first coupling means, such as in a plug and socket configuration. An example of this may be where the first coupling means is in the form of at least one protrusion and the second coupling means may be in the form of at least one depression. The actual number of the engaging coupling means may vary and may be anywhere from two matching parts, three matching parts, four matching parts and so on. The actual choice of matching parts may be dependent on the surface area of the first coupling means that is in contact with the tubular member, the flexibility of the tubular member, the thickness of the walls of the tubular member and so on. Such a choice of materials or design is obvious to the skilled person based on the teachings of the present invention, and the skilled person will recognize how to combine the design of the first coupling means and/or the second coupling means with the choice of material for the tubular member.

In one embodiment, the second coupling means may be at least one radially outwardly extending protrusion extending from an outer surface of the first coupling member. Such a protrusion may be in the form of a circumferential rim, a single protrusion which allows the first coupling means to engage the protrusion or in the form of two or more protrusions that are arranged circumferentially around the first coupling member, and may be spaced apart radially. The first coupling member may also be provided with a number of protrusions that are arranged along an axis that is parallel to the longitudinal axis of the catheter package. These longitudinally placed protrusions may provide a redundancy feature which means that if the first coupling means misses a first protrusion of the second coupling means, the first coupling means may engage with a second protrusion of the second coupling means.

In one embodiment of the present invention, the first coupling means and the second coupling means may be provided with cooperating protrusions. As an example, the first coupling member may be provided with asymmetrical protrusions in the radial direction while the second coupling member may be provided with symmetrical protrusions in the radial direction, or vice versa. This ensures that the protrusions of the first and the second coupling member will continuously have parts that are in cooperation with each other. The asymmetrical protrusions may advantageously be used to reduce the friction between the protrusion and the outer and/or inner surface of the tubular member.

The catheter assembly of the present invention may be provided as a gel-lubricated or a pre-wetted hydrophilic coated catheter assembly, where the gel or the wetting fluid may provide lubrication inside the catheter package. By providing such lubrication, the friction between the inner surface of the tubular member and the outer surface of the first coupling member may be reduced significantly, and this allows the first coupling member to move inside the tubular member without encountering a large frictional force. Thus, by having lubrication inside the tubular member the forces needed to extend the catheter out of the package may be reduced, and if combined with a reduced friction between the outer surface of the tubular member and the inner surface of the second coupling member the forces required to extend the catheter may be reduced even further.

In one embodiment of the present invention, the second coupling means may be a first distal and a second proximal area of the first coupling member having a diameter that is larger than the diameter of a central area of the first coupling member. Thus, the second coupling means may be in the form of two protrusions that are spaced apart in the longitudinal direction. The first coupling means may be arranged in between the two protrusions, allowing the second coupling member to engage the first coupling member in both directions on the longitudinal axis of the catheter assembly. This means that the second coupling member may both be used to extend the catheter out of the package and also for retracting the catheter back into the package after use. The specific design of the interaction of the second coupling member and the first coupling member may be varied from that described above, while ensuring that the second coupling member and the first coupling member engage in both directions.

In one embodiment of the present invention, an external diameter of the first coupling member may be larger than an internal diameter of the second coupling member. By providing the first coupling member as having a diameter that is larger than the internal diameter of the second coupling member, the second coupling member cannot pass the first coupling member in the longitudinal direction, and any movement of the second coupling member in a direction towards the first coupling member will push the first coupling member and move the first coupling member along with the second coupling member. The diameter of the first and/or the second coupling member need not be uniform in the radial direction, where it is advantageous that the diameter of the first and the second coupling is arranged in such a way that one coupling member is not capable of passing the other coupling member.

In one embodiment, the second coupling member may be provided with an external surface area providing gripping means for the user. As the user has to manoeuvre the second coupling member relative to the tubular member or the catheter package, the user may need to have an area on the second coupling member that is arranged to allow the second coupling member to be gripped. A number of users of urinary catheters have reduced dexterity in their hands and/or fingers and may have difficulty in gripping the second coupling member in order to extend the catheter out of the package. Thus, by providing a gripping area, which may be in the form of an ergonomic surface that increases the friction between the second coupling member and the skin surface that contacts the second coupling member, the use of the catheter assembly may be made easier for the user.

DETAILED DESCRIPTION OF THE DRAWING

Figure 1:
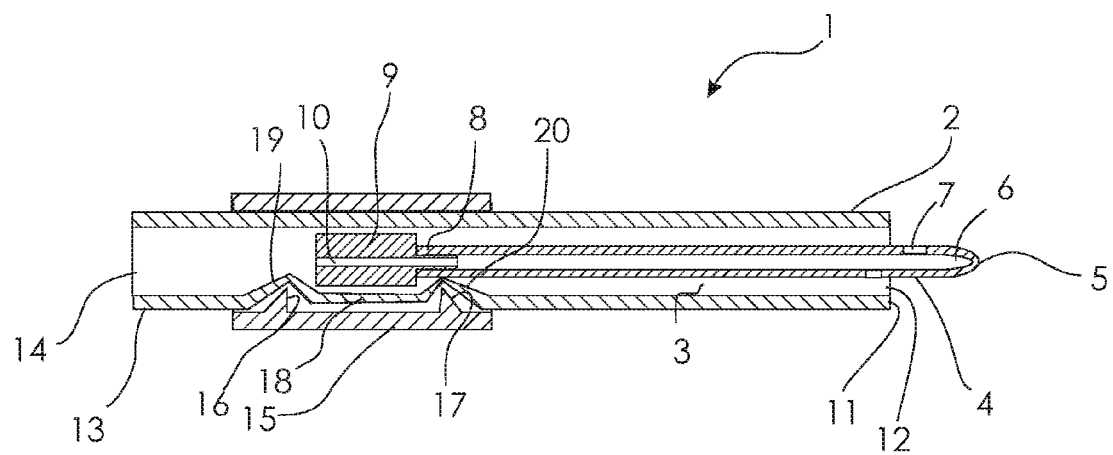
FIG. 1 shows a sectional side view of a catheter assembly according to the present invention.

FIG. 1 shows a sectional view of a catheter assembly 1 having a tubular member 2 defining a cavity 3 for containing a urinary catheter 4. The urinary catheter 4 has a proximal end 5 having an insertable tip that closes off an inner lumen 6 of the catheter for draining urine from a urinary bladder. The catheter 4 is provided with at least one opening 7 allowing urine to enter the inner lumen 6 of the catheter 4. The distal end 8 of the catheter 4 is provided with a first coupling member 9 which is provided with an inner lumen 10 that extends the inner lumen 6 of the catheter, and where the coupling member 9 is provided with a diameter that is larger than the diameter of the catheter 4.

The tubular member 2 has a proximal end 11 which is provided with an opening 12 that allows the catheter 4 to be extended out of the opening 12 and a distal end 13 having an opening 14 allowing for urine to be drained out of the catheter package 1 while the catheter 4 is extended inside the urethra of the user. During packaging of the catheter assembly 1 the distal end 13 and the proximal end 11 are closed, sealing the catheter 4 inside the tubular member 2. In advantageous embodiments of the catheter assembly, the closed tubular member may contain a gel and/or wetting fluid when the catheter 4 is a hydrophilic catheter, and the closed ends of the catheter assembly ensure that the gel or water does not exit the package during storage.

The catheter assembly is further provided with a second coupling member 15, which is allocated on the outer surface of the tubular member 2. The second coupling member is provided with a first coupling means 16 and 17 in the form of protrusions that reduce the diameter of the inner surface of the second coupling member by extending from the inner surface of the second coupling member. The second coupling member 15 is arranged on the tubular member 2 in such a way that the protrusions 16,17 bend the flexible wall 18 of the tubular member 2 and reduce the inner diameter of the tubular member 2 by transmitting the protrusions onto the tubular wall 19,20. When the first coupling member 9 is arranged between the two protrusions 16,17 in a longitudinal direction, the protrusions enclose the first coupling member 9, and when the second coupling member 15 is manoeuvred in the longitudinal direction the protrusions engage the first coupling member 9 through the flexible wall 18 of the tubular member 2 at the transmitted protrusions 19,20 and push the first coupling member 9 in the same direction as the second coupling member 15 is manoeuvred. This movement causes the catheter 4 to extend from the package when the second coupling member is manoeuvred in the direction towards the proximal end 11 of the tubular package 2 and the catheter 4 to retract into the tubular member 2 when the second coupling member is manoeuvred in the direction towards the distal end 13 of the tubular member 2.

The embodiment shown in FIG. 1 may be amended by providing a single protrusion 16 close to the distal end of the second coupling member 9 which allows the catheter 4 to be extended out of the package, where the second coupling member does not allow for the retraction of the catheter into the package, and the catheter assembly is discarded in an extended fashion.

Figure 2:
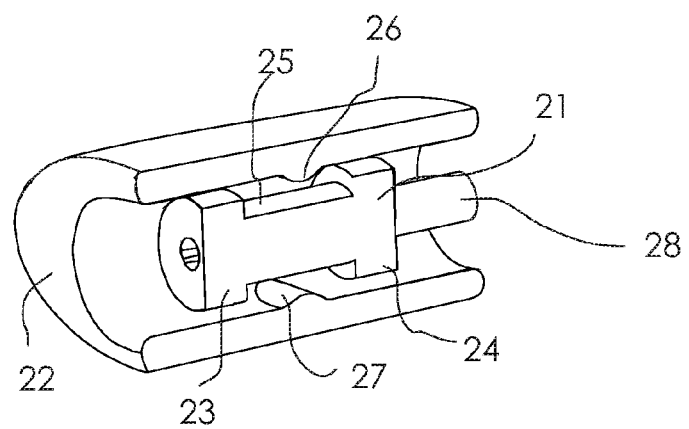
FIG. 2 shows a perspective sectional view of a first and a second coupling member according to the present invention.

FIG. 2 shows a perspective sectional view of an embodiment of a first coupling member 21 and a second coupling member 22 according to the present invention. The first and second coupling members are shown without the tubular member of the catheter assembly, for clarity, while in use the tubular member would be disposed between the two coupling members. The first coupling member is provided with a distal protrusion 23 and a proximal protrusion 24 and a central part 25 which has a diameter that is smaller than the distal and proximal protrusions. The second coupling member is provided with two diametrically opposed protrusions 26, 27 disposed on the inner surface 28 of the second coupling member 22. When the first and the second coupling members are arranged as shown in FIG. 2 in a combined position, the protrusions 26,27 of the second coupling member 22 are disposed between the distal 23 and the proximal protrusion 24 of the first coupling member 21. Thus, when the second coupling member is moved in a longitudinal direction along the tubular member (not shown) the protrusions 26,27 of the second coupling member 22 engage either the distal protrusion 23 or the proximal protrusion 24 of the first coupling member, and the movement of the second coupling member 22 is transferred to the first coupling member 21. In the embodiment shown in FIG. 2, the catheter may be connected to the first coupling member 21 using the connection member 28 which may be attached to the inner lumen of the catheter.

The form, positioning and number of the protrusions of the second coupling member may be varied provided that the protrusions transfer the movement of the second coupling member to the first coupling member.

Figure 3:
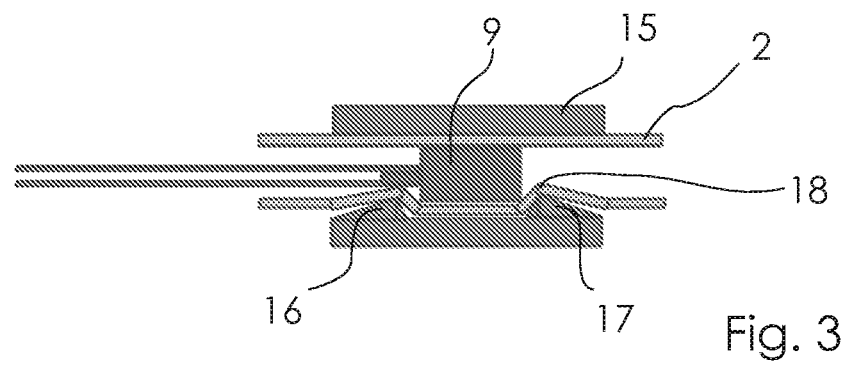
FIG. 3 shows a sectional side view of a catheter assembly according to the present invention.

FIG. 3 shows another embodiment of the present invention, similar to that shown in FIG. 1, where the protrusions 16,17 of the second coupling member are provided having a tapered angle at the surface area which abuts the first coupling member 9. This tapered surface angle increases the surface area of the protrusions that are in direct contact with the flexible wall 18 of the tubular member 2, and ensures that there are no sharp edges (=>90 degrees) that comes into contact with the tubular member. Thus, the protrusion will slide more easily along the tubular member as there will not be a sharp bend or fold in the flexible wall 18 of the tubular member 2. In this embodiment, the angle is set at approximately 75 degrees, however this angle may be varied to obtain a smooth transition between the protrusions and the tubular member.

Figure 4A:
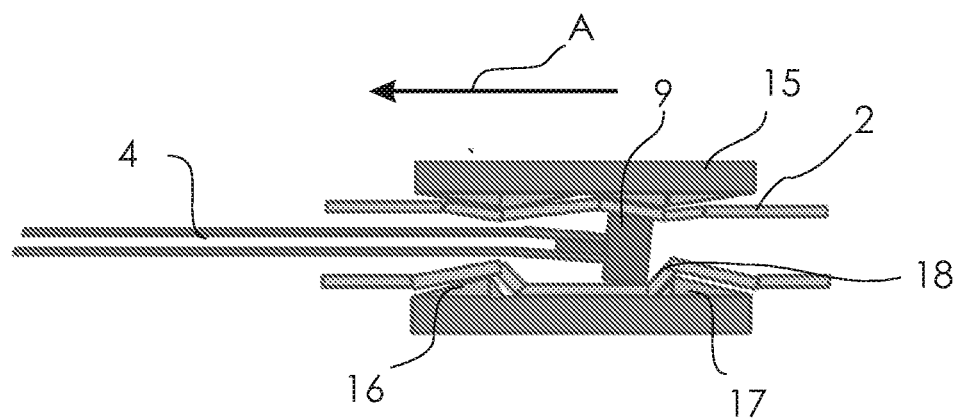
FIGS. 4a and 4b show a sectional side view of a catheter assembly according to the present invention showing the interaction between the first and the second coupling members.

FIG. 4a shows a sectional view of one embodiment of the present invention, where the second coupling member 15 is moved in a longitudinal direction A relative to the tubular member 2 to extend the catheter 4 out of the tubular member 2. The first coupling member 9 engages the distal protrusion 17 of the second coupling member 15 through the flexible wall 18 of the tubular member and the distal protrusion 17 transfers the forces used to move the second coupling member 15 to the first coupling member 9 and the catheter a extends out of the tubular member 2.

Figure 4B:
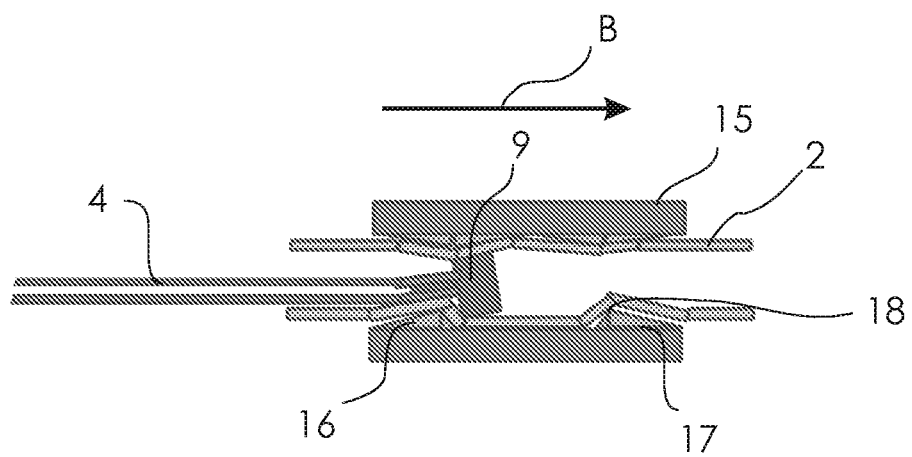

FIG. 4b shows a sectional view of one embodiment of the present invention, where the second coupling member 15 is moved in a longitudinal direction B relative to the tubular member to retract the catheter 4 back into the tubular member 2. The first coupling member 9 engages the proximal protrusion 17 of the second coupling member 15 through the flexible wall 18 and the forces required to move the second coupling member 15 are transferred to the first coupling member 9.

The invention claimed is:

1. A catheter assembly comprising
a urinary catheter having a proximal end for insertion into the urethra and a distal end comprising a first coupling member, the first coupling member having a central portion located between a distal prominence and a proximal prominence, where the central portion has a recess formed to have a diameter that is smaller than a diameter of either of the distal prominence and the proximal prominence,
a catheter package having a flexible wall with a proximal end and a distal end defining a longitudinal axis of the catheter package, where the catheter package comprises a cavity sized to receive the urinary catheter along the longitudinal axis of the catheter package, and where the proximal end of the catheter package has an opening sized for exposure of the proximal end of the urinary catheter, and
a second coupling member that is arranged on an outer surface of the catheter package,
wherein the second coupling member has a projection engaged within the recess of the first coupling member between the distal prominence and the proximal prominence through the flexible wall of the catheter package to allow the catheter to be manoeuvred along the longitudinal axis of the catheter package,
wherein the projection of the second coupling member is sized to provide a clearance distance between a protrusion in the flexible wall formed by the projection and the recess of the first coupling member.

2. The urinary catheter assembly according to claim 1, wherein the second coupling member has two diametrically opposed projections, with each of the two diametrically opposed projections engaged within the recess of the first coupling member.

3. The urinary catheter assembly according to claim 1, wherein the projection extends radially inward from an inner surface of the second coupling member.

4. The urinary catheter assembly according to claim 1, wherein a surface area of the second coupling member includes a low friction surface.

5. The urinary catheter assembly according to claim 1, wherein an external surface area of the second coupling member has a high-friction gripping surface.

6. A catheter assembly comprising:
   a urinary catheter having friction reducing lubricant, a proximal end for insertion into the urethra, and a distal end comprising a first coupling member, with the first coupling member having a recessed central portion located between a distal prominence and a proximal prominence;
   a catheter package having a flexible wall and defining a longitudinal axis between a proximal end and a distal end of the catheter package, where the catheter package has a cavity sized to receive the urinary catheter along the longitudinal axis of the catheter package, and where the proximal end of the catheter package has an opening sized for exposure of the proximal end of the urinary catheter; and
   a second coupling member that is arranged on an outer surface of the catheter package;
   wherein the second coupling member has a projection configured to engage in the recessed central portion of the first coupling member through the flexible wall of the catheter package;
   wherein the projection of the second coupling member is sized to provide a clearance distance between a protrusion formed through the flexible wall from the projection and the friction reducing lubricant of the urinary catheter.

\* \* \* \* \*